(12) United States Patent
Chang et al.

(10) Patent No.: US 6,413,516 B1
(45) Date of Patent: *Jul. 2, 2002

(54) PEPTIDES AND METHODS AGAINST PSORIASIS

(75) Inventors: Jennie C. C. Chang, San Marcos; Steven W. Brostoff, Carlsbad; Dennis J. Carlo, Rancho Santa Fe, all of CA (US)

(73) Assignee: The Immune Response Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/182,967

(22) Filed: Jan. 14, 1994

Related U.S. Application Data

(63) Continuation-in-part of application No. 07/813,867, filed on Dec. 14, 1991, now abandoned, which is a continuation-in-part of application No. 07/644,611, filed on Jan. 22, 1991, now abandoned, which is a continuation-in-part of application No. 07/530,229, filed on May 30, 1990, now abandoned, which is a continuation-in-part of application No. 07/382,085, filed on Jul. 18, 1989, now abandoned, and a continuation-in-part of application No. 07/382,086, filed on Jul. 18, 1989, now abandoned, which is a continuation-in-part of application No. 07/326,314, filed on Mar. 21, 1989, now abandoned.

(51) Int. Cl.$^7$ .............................................. A61K 39/00
(52) U.S. Cl. ................................ 424/185.1; 424/184.1; 530/328; 530/350; 514/12; 514/13; 514/14; 514/15
(58) Field of Search .......................... 424/185.1, 184.1, 424/278.1, 93.71; 514/12–15; 530/300, 350, 395, 868; 435/69.3, 7.1, 6, 320.1; 536/23.5, 24.31

(56) References Cited

U.S. PATENT DOCUMENTS

| | | | |
|---|---|---|---|
| 4,886,743 A | * | 12/1989 | Hood |
| 5,840,304 A | * | 11/1998 | Davis et al. |

FOREIGN PATENT DOCUMENTS

| | | |
|---|---|---|
| WO | WO 93/06135 | 1/1993 |

OTHER PUBLICATIONS

Ulmer, J.B. Current Opinion Drug Disc. Devel. 4(2):192–197, 2001.*
Borgato et al. Clin & Exp. Rheum 15:475–479 Desquenne–Clark et al. PNAS 88:7219–7723, 1997, 1991.*
Anderson Nature 392:26–30 Hafler et al. Immunol Today 17:152–159, 1998, 1996.*
The Merck Manual Beers ed. 816–818, 1999.*
Li et al. J. Exp. Med. 174:1537, 1991.*
Sakai et al. PNAS 86 9470, 1989*
Kalin et al J. Exp. Med. 150: 2222, 1994.*
Wofsy et al. J. Exp. Med. 161:378, 1985.*
Ranges et al. J. Exp. Med. 162: 1105, 1985.*
Wooley et al J. Immunology 134:2366, 1985.*
Hafler, D. A. et al., Immunology Today 17(4):152–159 (1996), "TCR usage in human and experimental demyelinating disease". Apr. 1996.*
Lewis et al. "Restricted T cell receptor Vβ gene usage in the skin of patients with guttate and chronic plaque psoriasis" Brit. J. Derm., 129:514–520 (1993).
Leung et al, "A potential role for superantigens in the pathogenesis of psoriasis" J. of Investigative Dermatology 93:225–228 (1993).
Posnett et al. "Analysis of T cell receptor idiotypes in autoimmune diseases." Clinical Research 36(3):445A (1988).
Kimura et al., Sequences and repertoire of the human T cell receptor α and β chain variable region genes in thymocytes. Eur. J. Immunol. 17:375–383 (1987).
Sedgwick, J., Long–term depletion of CD8 T cells in vivo in the rat: no observed role for CD8 (cytotoxic/suppressor) cells in the immunoregulatin of experimental allergic encephalomyelitis. Eur. J. Immunol. 18:495–502 (1988).
Urban et al., Restricted use of T cell receptor V genes in murine autoimmune encephalomyelitis raises possibilites for antibody therapy. Cell 54:577–592 (1988).
Lider et al., Anti–idiotypic network induced by T cell vaccination against experimental autoimmune encephalobyelitis. Science 239:181–183 (1988).
Sun et al., Suppression of experimentally induced autoimmune encephalmyelitis by cytolytic T–T cell interactions. Nature 332:843–845 (1988).
Offner et al., Lymphocyte vaccination against experimental autoimmune encephalomyelitis: evaluation of vaccination protocols. J. Neuroimmunol. 21:13–22 (1989).
Choi et al., Interaction of *Staphylococcus aureus* toxin "superantigens" with human T cells. Proc. Natl. Acad. Sci. USA 86:8941–8945 (1989).

(List continued on next page.)

Primary Examiner—Patrick J. Nolan
Assistant Examiner—Gerald R. Ewoldt
(74) Attorney, Agent, or Firm—Campbell & Flores LLP

(57) ABSTRACT

This invention relates to methods of preventing or reducing the severity of psoriasis. In one embodiment, the method involves administering to the individual a peptide having substantially the sequence of a non-conserved region sequence of a T cell receptor, present on the surface of T cells mediating psoriasis or a fragment thereof, wherein the peptide or fragment is capable of causing an effect on the immune system to regulate the T cells. In particular, the T cell receptor has the Vβ region-Vβ3, Vβ13.1 or Vβ17. In another embodiment, the method involves gene therapy. The invention also relates to methods of diagnosing psoriasis by determining the presence of psoriasis predominant T cell receptors.

13 Claims, 1 Drawing Sheet

OTHER PUBLICATIONS

White et al., The Vβ–specific superantigen staphylococcal enterotoxin B: stimulation of mature T cells and clonal deletion in neonatal mice. Cell 56:27–35 (1989).

Pullen et al., Identification of the region T cell receptor β chain that interacts with the self–superantigen Mls–1. Cell 61:1365–1374 (1990).

Janeway, C., Self superantigens? Cell 63:659–661 (1990).

Marrack and Kappler, The staphylococcal enterotoxins and their relatives. Science 248:705–711 (1990).

Ratner, Can the antisense message be delivered? *Biotechnology* 7:207 (1989).

Simons et al., Antisense c–myb oligonucleotides inhibit intimal arterial smooth muscle cell accumlation in vivo. *Nature* 359:67–70 (1992).

Cooper et al., Mechanisms of cyclosperin A inhibition of antigen presenting activity in uninvolved and lesional psoriatic epidermis. *J. Invest. Dermatol* 94:649–656 (1990).

Wong et al., The mechanisms of action of cyclosporin A in the treatment of psoriasis. *Immunology Today* 14:69–74 (1993).

Valdimarsson et al., Psoriasis: a disease of abnormal keratinocyte proliferation induced by T lymphocytes. *Immunology Today* 7:256–259 (1986).

Breathnach, "The skin immune system and psoriasis." *Clin. Exp. Immunol.* 91:343–345 (1993).

Paukkonen et al., The development of manifest psoriatic lesions is linked with the invasions of $CD8^{30}$ T cells and $CD11c^+$ macrophages into the epidermis. *Arch. Dermatol. Res.* 284:375–379 (1992).

McMillan, Blood and tissue analysis of T–cell subsets in cutaneous diseases. *J. Cut. Path.* 9:55–59 (1983).

Baker et al., Intralesional cyclosporin in psoriasis: effects on T lymphocyte and dendritic cell subpopulations. *Br. J. Dematol.* 120:207–213 (1989).

Griffiths and Voorhees, Immunological mechanisms involved in psoriasis. *Springer Semin. Immunopathol.* 13:441–454 (1992).

\* cited by examiner

Figure 1

|      | CDR1 | CDR2 | CDR4 |
|------|------|------|------|
| Vβ3    | DVKVTQSSRYLVKRTGEKVFLECVQDMDHENMFWYRQDPGLGLRLIYFSYDVKMKEKGDIPEGYSVSREKKERFSLILESASTNQTSMYLCASS |
| Vβ13.1 | NAGVTQTPKFQVLKTGQSMTLQCAQDMNHEYMSWYRQDPGMGLRLIHYSVGAGITDQGEVPNGYNVSRSTTEDFPLRLLSAAPSQTSVYFCASS |
| Vβ17   | DGGITQSPKYLFRKEGQNVTLSCEQNLNHDAMYWYRQDPGQGLRLIYYSQIVNDFQKGDIAEGYSVSREKKESFPLTVTSAQKNPTAFYLCASS | ns

SEQUENCE LISTING (1) GENERAL INFORMATION:

(iii) NUMBER OF SEQUENCES: 34

(2) INFORMATION FOR SEQ ID NO:1:

(i) SEQUENCE CHARACTERISTICS:
      (A) LENGTH: 94 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:1:

```
Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
                20                  25                  30

Phe Trp Tyr Arg Gln Asp Pro Gly Leu Gly Leu Arg Leu Ile Tyr Phe
            35                  40                  45

Ser Tyr Asp Val Lys Met Lys Glu Lys Gly Asp Ile Pro Glu Gly Tyr
        50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser
                85                  90
```

(2) INFORMATION FOR SEQ ID NO:2:

(i) SEQUENCE CHARACTERISTICS:
      (A) LENGTH: 94 amino acids
      (B) TYPE: amino acid
      (C) STRANDEDNESS:
      (D) TOPOLOGY: linear (xi) SEQUENCE DESCRIPTION: SEQ ID NO:2:

```
Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
                20                  25                  30

Ser Trp Tyr Arg Gln Asp Pro Gly Met Gly Leu Arg Leu Ile His Tyr
            35                  40                  45

Ser Val Gly Ala Gly Ile Thr Asp Gln Gly Glu Val Pro Asn Gly Tyr
        50                  55                  60

Asn Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Ser
                85                  90
```

(2) INFORMATION FOR SEQ ID NO:3:

(i) SEQUENCE CHARACTERISTICS:
        (A) LENGTH: 94 amino acids
        (B) TYPE: amino acid
        (C) STRANDEDNESS:
        (D) TOPOLOGY: linear (xi) SEQUENCE DESCRIPTION: SEQ ID NO:3:

```
Asp Gly Gly Ile Thr Gln Ser Pro Lys Tyr Leu Phe Arg Lys Glu Gly
 1               5                  10                  15

Gln Asn Val Thr Leu Ser Cys Glu Gln Asn Leu Asn His Asp Ala Met
             20                  25                  30

Tyr Trp Tyr Arg Gln Asp Pro Gly Gln Gly Leu Arg Leu Ile Tyr Tyr
         35                  40                  45

Ser Gln Ile Val Asn Asp Phe Gln Lys Gly Asp Ile Ala Glu Gly Tyr
 50                  55                  60

Ser Val Ser Arg Glu Lys Lys Glu Ser Phe Pro Leu Thr Val Thr Ser
 65                  70                  75                  80

Ala Gln Lys Asn Pro Thr Ala Phe Tyr Leu Cys Ala Ser Ser
                 85                  90
```

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:4:

GCGGCTGCTC AGGCAGTA                                        18

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:5:

TCAGGTGTGA TCCAATTTC                                      19

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:6:

TCTGGTACAG ACAGACCATG AT                                 22

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:7:

GATACTGACA AAGGAGAAGT CTCAGAT                           27

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:8:

TCACAGATAG TAAATGACTT TCAG                                              24

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:9:

TTGGGTGTGG GAGATCTCTG C                                                 21

(2) INFORMATION FOR SEQ ID NO:10:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:10:

Cys Ala Thr Arg Glu Val Ala Gly Leu Ser Val Thr Asp Thr Gln
1               5                   10                  15

(2) INFORMATION FOR SEQ ID NO:11:

(i) SEQUENCE CHARACTERISTICS:
        (A) LENGTH: 13 amino acids
        (B) TYPE: amino acid
        (C) STRANDEDNESS:
        (D) TOPOLOGY: linear (xi) SEQUENCE DESCRIPTION: SEQ ID NO:11:

Cys Ala Ser Ser Tyr Ser Ser Val Leu Asn Thr Glu Ala
1               5                   10

(2) INFORMATION FOR SEQ ID NO:12:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO:12:

Cys Ala Ser Ser Leu Asn Ser Leu Asn Thr Glu Ala
1               5                   10

(2) INFORMATION FOR SEQ ID NO:13:

(i) SEQUENCE CHARACTERISTICS:
        (A) LENGTH: 14 amino acids
        (B) TYPE: amino acid
        (C) STRANDEDNESS:
        (D) TOPOLOGY: linear (xi) SEQUENCE DESCRIPTION: SEQ ID NO:13:

Cys Ala Ser Ala Pro Tyr Gln Asp Ser Thr Tyr Glu Gln Tyr
1               5                   10

(2) INFORMATION FOR SEQ ID NO:14:

(i) SEQUENCE CHARACTERISTICS:
        (A) LENGTH: 18 amino acids
        (B) TYPE: amino acid
        (C) STRANDEDNESS:
        (D) TOPOLOGY: linear (xi) SEQUENCE DESCRIPTION: SEQ ID NO:14:

Cys Ala Ser Ser Pro His Val Leu Ala Gly Ala Ser Gly Gly Tyr Asn
1               5                   10                  15

Glu Gln (2) INFORMATION FOR SEQ ID NO:15:

(i) SEQUENCE CHARACTERISTICS:
        (A) LENGTH: 13 amino acids
        (B) TYPE: amino acid
        (C) STRANDEDNESS:
        (D) TOPOLOGY: linear (xi) SEQUENCE DESCRIPTION: SEQ ID NO:15:

Cys Ala Ser Ser Pro Leu Gly Val Gly Asn Thr Ile Tyr
1               5                   10

(2) INFORMATION FOR SEQ ID NO:16:

(i) SEQUENCE CHARACTERISTICS:
        (A) LENGTH: 13 amino acids
        (B) TYPE: amino acid
        (C) STRANDEDNESS:
        (D) TOPOLOGY: linear (xi) SEQUENCE DESCRIPTION: SEQ ID NO:16:

Cys Ala Ser Ser Tyr Ser Thr Gly Gly Asn Glu Gln Phe
1               5                   10

(2) INFORMATION FOR SEQ ID NO:17:

(i) SEQUENCE CHARACTERISTICS:
        (A) LENGTH: 11 amino acids
        (B) TYPE: amino acid
        (C) STRANDEDNESS:
        (D) TOPOLOGY: linear (xi) SEQUENCE DESCRIPTION: SEQ ID NO:17:

Cys Ala Ser Leu Gly Val Met Asn Thr Glu Ala
1               5                   10

(2) INFORMATION FOR SEQ ID NO:18:

(i) SEQUENCE CHARACTERISTICS:
        (A) LENGTH: 16 amino acids
        (B) TYPE: amino acid
        (C) STRANDEDNESS:
        (D) TOPOLOGY: linear (xi) SEQUENCE DESCRIPTION: SEQ ID NO:18:

Cys Ala Ser Ser Ser Leu Pro Arg Phe Gly Gln Asp Thr Gly Glu Leu
1               5                   10                  15

(2) INFORMATION FOR SEQ ID NO:19:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO:19:

Cys Ala Ser Ser Leu Glu Gly Ile Asn Ile Gln Tyr
1            5                 10

(2) INFORMATION FOR SEQ ID NO:20:

(i) SEQUENCE CHARACTERISTICS:
        (A) LENGTH: 11 amino acids
        (B) TYPE: amino acid
        (C) STRANDEDNESS:
        (D) TOPOLOGY: linear (xi) SEQUENCE DESCRIPTION: SEQ ID NO:20:

Cys Ala Thr Asn Thr Glu Gly Ser Tyr Glu Gln
1            5                 10

(2) INFORMATION FOR SEQ ID NO:21:

(i) SEQUENCE CHARACTERISTICS:
        (A) LENGTH: 13 amino acids
        (B) TYPE: amino acid
        (C) STRANDEDNESS:
        (D) TOPOLOGY: linear (xi) SEQUENCE DESCRIPTION: SEQ ID NO:21:

Cys Ala Ser Ser Pro Asn Arg Val Ser Ser Tyr Asn Glu
1            5                 10

(2) INFORMATION FOR SEQ ID NO:22:

(i) SEQUENCE CHARACTERISTICS:
        (A) LENGTH: 14 amino acids
        (B) TYPE: amino acid
        (C) STRANDEDNESS:
        (D) TOPOLOGY: linear (xi) SEQUENCE DESCRIPTION: SEQ ID NO:22:

Cys Ala Ser Ser Tyr Arg Ala Gly Gly Leu Asp Thr Gln Tyr
1            5                 10

(2) INFORMATION FOR SEQ ID NO:23:

(i) SEQUENCE CHARACTERISTICS:
        (A) LENGTH: 14 amino acids
        (B) TYPE: amino acid
        (C) STRANDEDNESS:
        (D) TOPOLOGY: linear (xi) SEQUENCE DESCRIPTION: SEQ ID NO:23:

Cys Ala Ser Ser Val Pro Gly Pro Thr Asn Thr Glu Ala Phe
1            5                 10

(2) INFORMATION FOR SEQ ID NO:24:

(i) SEQUENCE CHARACTERISTICS:
        (A) LENGTH: 14 amino acids
        (B) TYPE: amino acid
        (C) STRANDEDNESS:
        (D) TOPOLOGY: linear (xi) SEQUENCE DESCRIPTION: SEQ ID NO:24:

Cys Ala Ser Gly Thr Gly Leu Thr Ser Pro Gly Glu Leu Phe
1               5                   10

(2) INFORMATION FOR SEQ ID NO:25:

(i) SEQUENCE CHARACTERISTICS:
            (A) LENGTH: 17 amino acids
            (B) TYPE: amino acid
            (C) STRANDEDNESS:
            (D) TOPOLOGY: linear (xi) SEQUENCE DESCRIPTION: SEQ ID NO:25:

Cys Ala Ser Ser Ile Asn Thr Arg Ala Ser Gly Arg His Tyr Glu Gln
1               5                   10                  15

Phe (2) INFORMATION FOR SEQ ID NO:26:

(i) SEQUENCE CHARACTERISTICS:
            (A) LENGTH: 13 amino acids
            (B) TYPE: amino acid
            (C) STRANDEDNESS:
            (D) TOPOLOGY: linear (xi) SEQUENCE DESCRIPTION: SEQ ID NO:26:

Cys Ala Ser Ser Ile Pro Gly Arg Gly Tyr Gly Tyr Thr
1               5                   10

(2) INFORMATION FOR SEQ ID NO:27:

(i) SEQUENCE CHARACTERISTICS:
            (A) LENGTH: 17 amino acids
            (B) TYPE: amino acid
            (C) STRANDEDNESS:
            (D) TOPOLOGY: linear (xi) SEQUENCE DESCRIPTION: SEQ ID NO:27:

Cys Ala Ser Arg Pro Gly Gly Gly Pro Ala Thr Ile Ala Asn Glu Gln
1               5                   10                  15

Phe (2) INFORMATION FOR SEQ ID NO:28:

(i) SEQUENCE CHARACTERISTICS:
            (A) LENGTH: 16 amino acids
            (B) TYPE: amino acid
            (C) STRANDEDNESS:
            (D) TOPOLOGY: linear (xi) SEQUENCE DESCRIPTION: SEQ ID NO:28:

Cys Ala Ser Arg Glu Leu Gly Gln Ile Phe Gly Val Glu Lys Leu Phe
1               5                   10                  15

(2) INFORMATION FOR SEQ ID NO:29:

(i) SEQUENCE CHARACTERISTICS:
            (A) LENGTH: 15 amino acids
            (B) TYPE: amino acid
            (C) STRANDEDNESS:
            (D) TOPOLOGY: linear (xi) SEQUENCE DESCRIPTION: SEQ ID NO:29:

Cys Ala Ser Ser Gln Ser Gly Gly Asn Tyr Arg Glu Gln Tyr Phe
1               5                   10                  15

(2) INFORMATION FOR SEQ ID NO:30:

(i) SEQUENCE CHARACTERISTICS:
        (A) LENGTH: 13 amino acids
        (B) TYPE: amino acid
        (C) STRANDEDNESS:
        (D) TOPOLOGY: linear (xi) SEQUENCE DESCRIPTION: SEQ ID NO:30:

```
Cys Ala Ser Ser Arg Thr Leu Gly Trp Glu Gln Tyr Phe
1               5                   10
```

(2) INFORMATION FOR SEQ ID NO:31:

(i) SEQUENCE CHARACTERISTICS:
        (A) LENGTH: 14 amino acids
        (B) TYPE: amino acid
        (C) STRANDEDNESS:
        (D) TOPOLOGY: linear (xi) SEQUENCE DESCRIPTION: SEQ ID NO:31:

```
Cys Ala Ser Ser Glu Asp Gly Gly Leu Gly Thr Glu Ala Phe
1               5                   10
```

(2) INFORMATION FOR SEQ ID NO:32:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:32:

```
Cys Ala Thr Leu Ala Gly Thr Gly Met Arg Asn Glu Gln Tyr Phe
1               5                   10                  15
```

(2) INFORMATION FOR SEQ ID NO:33:

(i) SEQUENCE CHARACTERISTICS:
        (A) LENGTH: 14 amino acids
        (B) TYPE: amino acid
        (C) STRANDEDNESS:
        (D) TOPOLOGY: linear (xi) SEQUENCE DESCRIPTION: SEQ ID NO:33:

```
Cys Ala Ser Ser Leu Thr Pro Ser Gly Gly Ser Tyr Glu Gln
1               5                   10
```

(2) INFORMATION FOR SEQ ID NO:34:

(i) SEQUENCE CHARACTERISTICS:
        (A) LENGTH: 11 amino acids
        (B) TYPE: amino acid
        (C) STRANDEDNESS:
        (D) TOPOLOGY: linear (xi) SEQUENCE DESCRIPTION: SEQ ID NO:34:

```
Cys Ala Ser Leu Gly Val Leu Asn Thr Glu Ala
1               5                   10
```

PEPTIDES AND METHODS AGAINST PSORIASIS

This application is a continuation-in part of U.S. Ser. No. 07/813,867, filed Dec. 14, 1991, now abandoned, which is a continuation-in-part of U.S. Ser. No. 07/644,611, filed Jan. 22, 1991, now abandoned, which is a continuation-in-part of U.S. Ser. No. 07,/530,229, filed May 30, 1990, now abandoned, which is a continuation-in-part of U.S. Ser. Nos. 07/382,085 and 07/382,086, both filed on Jul. 18, 1989, both now abandoned, which are continuations-in-part of U.S. Ser. No. 07/3,26,314, filed Mar. 21, 1989, now abandoned. The contents of all such related applications are incorporated herein by reference in their entirety.

BACKGROUND OF THE INVENTION

This invention relates to the immune system and, more specifically, to methods of modifying pathological immune responses in psoriasis.

Higher organisms are characterized by an immune system which protects them against invasion by potentially-deleterious substances or microorganisms. When a substance, termed an antigen, enters the body, and is recognized as foreign, the immune system mounts both an antibody-mediated response and a cell-mediated response. Cells of the immune system termed B lymphocytes, or B cells, produce antibodies that specifically recognize and bind to the foreign substance. Other lymphocytes termed T lymphocytes, or T cells, both effect and regulate the cell-mediated response resulting eventually in the elimination of the antigen.

A variety of T cells are involved in the cell-mediated response. Some induce particular B cell clones to proliferate and produce antibodies specific for the antigen. Others recognize and destroy cells presenting foreign antigens on their surfaces. Certain T cells regulate the response by either stimulating or suppressing other cells.

While the normal immune system is closely regulated, aberrations in immune response are not uncommon. In some instances, the immune system functions inappropriately and reacts to a component of the host as if it were, in fact, foreign. Such a response results in an autoimmune disease, in which the host's immune system attacks the host's own tissue. T cells, as the primary regulators of the immune system, directly or indirectly effect such autoimmune pathologies.

Psoriasis is characterized by epidermal keratinocyte hyperproliferation, coupled with an inflammatory infiltrate. The pathogenesis of this disease is not fully understood. T cell activation appears to play a vital role in triggering and/or maintaining the disease. As evidence, cyclosporin A works effectively on improving the patient's condition.

A need exists for improved and effective means of curing or ameliorating psoriasis. Such a treatment should ideally control the inappropriate T cell response, rather than merely reducing the symptoms. The present invention satisfies this need and provides related advantages as well.

SUMMARY OF THE INVENTION

This invention provides methods of preventing or reducing the severity of psoriasis in an individual by administering a peptide having substantially the sequence of a T cell receptor present on the surface of T cells mediating psoriasis which is capable of causing an effect on the immune system to regulate the T cells.

This invention provides methods of preventing or reducing the severity of psoriasis in an individual by administering a peptide having substantially the sequence of a non-conserved region sequence of a T cell receptor present on the surface of T cells mediating psoriasis or a fragment thereof, wherein the peptide or fragment is capable of causing an effect on the immune system to regulate the T cells.

This invention also provides compositions for preventing or reducing the severity of psoriasis in an individual having a peptide having substantially the sequence of a non-conserved region of a T cell receptor present on the surface of T cells mediating psoriasis or a fragment thereof, wherein the peptide or fragment is capable of causing an effect on the immune system to regulate the T cells.

In another embodiment, this invention concerns methods of preventing the proliferation of T cells associated with psoriasis in an individual by determining a T cell receptor binding partner for a T cell receptor present on the surface of T cells mediating psoriasis and administering the T cell binding partner to the individual.

According to another embodiment, the method involves preventing or reducing the severity of psoriasis by inhibiting the binding of a T cell receptor to its TCR binding partner in order to prevent the proliferation of T cells associated with psoriasis.

This invention also provides methods of preventing or reducing the severity of psoriasis in an individual by contacting T cells specifically associated with psoriasis with an effective amount of a cytotoxic or cytostatic agent specifically reactive with such T cells to inhibit their activity.

This invention further provides methods of diagnosing or predicting susceptibility to psoriasis in an individual by detecting T cells having a T cell receptor associated with psoriasis in a sample from the individual, the presence of abnormal expression of T cells containing the T cell receptor indicating the pathology or susceptibility to psoriasis.

This invention provides methods of preventing or reducing the severity of psoriasis in an individual by preventing the attachment of a psoriasis-associated T-cell receptor to its binding partner.

Another method of this invention involves preventing or reducing the severity of psoriasis in an individual by administering to the individual a vector having an expression control sequence operatively linked to a nucleic acid encoding a T cell receptor or a peptide having substantially the sequence of a non-conserved region sequence of a T cell receptor present on the surface of T cells mediating psoriasis or a fragment thereof, wherein the peptide or fragment is capable of causing an effect on the immune system to regulate the T cells.

This invention also provides vectors having an expression control sequence operatively linked to a nucleic acid encoding a T cell receptor or a peptide having substantially the sequence of a non-conserved region sequence of a T cell receptor present on the surface of T cells mediating psoriasis.

BRIEF DESCRIPTION OF THE FIGURE

FIG. 1 shows the variable region sequences of Vβ3 (SEQ ID NO: 1), Vβ13.1 (SEQ ID NO: 2) and Vβ17 (SEQ ID NO: 3). The underlined segments depict the CDR1, CDR2 and CDR4 hypervariable regions of each Vβ chain. The sequences between the CDR2 and CDR4 regions represent an overlap between these two hypervariable regions.

DETAILED DESCRIPTION OF THE INVENTION

This invention provides compositions and methods for preventing or reducing the severity of psoriasis. The invention results from the discovery that psoriasis is characterized by the predominant usage of certain T cell receptors in the psoriatic plaque lesion. In particular, Vβ3, Vβ13.1 and Vβ17 predominate. Treatment according to the method of the invention provides a specific and sustained amelioration which avoids problems associated with other potential avenues of therapy.

As used herein, "substantially the amino acid sequence," or "substantially the sequence" when referring to an amino acid sequence means the described sequence or other sequences having any additions, deletions or substitutions that do not substantially effect the ability of the sequence to cause an effect on the immune system which regulates T cells having the desired T cell receptor. Such sequences commonly have many other sequences adjacent to the described sequence.

A portion or segment of the described sequence can be used so long as it is sufficiently characteristic of the desired T cell receptor or fragment thereof to cause an effect on the immune system which regulates T cells having the desired T cell receptors, but not against T cells not having desired T cell receptors. Such variations in the sequence can easily be made, for example by synthesizing an alternative sequence. The alternate sequence can then be tested, for example by administration to a vertebrate, to determine its effectiveness.

As used herein, the term "fragment" means a subset of the non-conserved amino acid sequence of a TCR that can cause an effect on the immune system which regulates T cells. As used herein, the term "non-conserved region" refers to variable and VDJ regions. The term is intended to include such fragments in conjunction with or combined with additional sequences or moieties, as for example where the peptide is coupled to other amino acid sequences or to a carrier. The terms "fragment" and "peptide" can, therefore, be used interchangeably since a peptide will be the most common fragment of the T cell receptor. Each fragment of the invention can have an altered sequence, as described above for the term "substantially the sequence."

Reference herein to a "fragment," "portion" or "segment" of a T cell receptor does not mean that the composition must be derived from intact T cell receptors. Such "fragments," portions" or "segments" can be produced by various means well-known to those skilled in the art, such as, for example, manual or automatic peptide synthesis, various methods of cloning or enzymatic treatment of a whole TCR.

As used herein, the phrase to "cause an effect on the immune system which regulates T cells" means to cause the immune system to modify the activity in response to their ligands of T cells bearing particular T cell receptors. Such an effect can include either wholly or partially a T cell response. For example, the down regulation of an autoreactive T cell may be a result of the recognition by a regulatory T cell of the T cell receptor peptide in the groove of an MHC molecule on the surface of an autoreactive T cell. Alternatively, the regulatory effect can be caused by the interference by a T cell receptor peptide of the interaction of a T cell recptor on an autoreactive T cell and its MHC/peptide ligand. Such modification of activity can be evidenced by amelioration of the severity of inflammation in the target tissue. The amount of such a peptide necessary to cause such an effect will vary between species and individuals depending on many factors which one skilled in the art can determine.

As used herein, "binding partner" means a compound which is reactive with a TCR. Generally, this compound will be a Major Histocompatibility Antigen (MHC) but can be any compound capable of directly or indirectly stimulating T cell activation or proliferation when bound to the TCR. Such compounds can also be, for example, a superantigen that binds to a superantigen binding site on the TCR.

As used herein, "superantigens" means antigens or fragments thereof that bind preferentially to T cells at specific sites on the β chain of a TCR and stimulate T cells at very high frequency rate. Such superantigens can be endogenous or exogenous. "Frequency" refers to the proportion of T cells responding to antigens and ranges from about 1/5 to 1/100 in response to superantigens. Thus, superantigens are distinguishable from conventional antigens, which have a much lower T cell response frequency rate ranging from about $1/10^4$ to $1/10^6$. Superantigens activate T cells by binding to specific Vβs. The superantigen binding sites of various TCRs have been distinguished from the conventional hypervariable regions (CDRs) of TCRs. These CDRs represent the regions of TCRs thought to be responsible for binding conventional antigens that are complexed to MHC.

As used herein, "ligand" means any molecule that reacts with another molecule to form a complex.

As used herein, "selectively binds" means that a molecule binds to one type of molecule or related group of molecules, but not substantially to other types of molecules. In relation to Vβs, "selective binding" indicates binding to TCRs or fragments thereof containing a specific Vβ without substantial cross-reactivity with other TCRs that lack the specific Vβ.

As used herein, "individual" means any vertebrate, including human, capable of having psoriasis.

As used herein, "reduce the severity of psoriasis" means improving the condition of psoriatic lesions or decreasing the percentage of T cell's in a lesion bearing a preferential T cell receptor.

The immune system is the primary biological defense of the host (self) against potentially pernicious agents (non-self). These pernicious agents may be pathogens, such as bacteria or viruses, as well as modified self cells, including virus-infected cells, tumor cells or other abnormal cells of the host. Collectively, these targets of the immune system are referred to as antigens. The recognition of antigen by the immune system rapidly mobilizes immune mechanisms to destroy that antigen, thus preserving the sanctity of the host environment.

T cells owe their antigen specificity to the T cell receptor (TCR) which is expressed on the cell surface. The TCR is a heterodimeric glycoprotein, composed of two polypeptide chains, each with a molecular weight of approximately 45 kD. Two forms of the TCR have been identified. One is composed of an alpha chain and a beta chain, while the second consists of a gamma chain and a delta chain. Each of these four TCR polypeptide chains is encoded by a distinct genetic locus containing multiple discontinuous gene segments. These include variable (V) region gene segments, joining (J) region gene segments and constant (C) region gene segments. Beta and delta chains contain an additional element termed the diversity (D) gene segment. Since D segments and elements are found in only some of the TCR genetic loci, and polypeptides, further references herein to D segments and elements will be in parentheses to indicate the inclusion of these regions only in the appropriate TCR chains. Thus, V(D)J refers either to VDJ sequences of chains which have a D region or refers to VJ sequences of chains lacking D regions.

With respect to the variable region of the beta chain, referred to as a Vβ, the nomenclature used herein to identify specific Vβs follows that of Kimura et al., *Eur. J. Immuno.* 17:375–383 (1987).

During lymphocyte maturation, single V, (D) and J gene segments are rearranged to form a functional gene that determines the amino acid sequence of the TCR expressed by that cell. Since the pool of V, (D) and J genes which may be rearranged is multi-membered and since individual members of these pools may be rearranged in virtually any combination, the complete TCR repertoire is highly diverse and capable of specifically recognizing and binding the vast array of binding partners to which an organism may be exposed. However, a particular T cell will have only one TCR molecule and that TCR molecule, to a large degree if not singly, determines the specificity of that T cell for its binding partner.

Animal models have contributed significantly to the understanding of the immunological mechanisms of autoimmune disease. One such animal model, experimental allergic encephalomyelitis (EAE), is an autoimmune disease of the central nervous system that can be induced in mice and rats by immunization with myelin basic protein (MBP). The disease is characterized clinically by paralysis and mild wasting and histologically by a perivascular mononuclear cell infiltration of the central nervous system parenchyma. The disease pathogenesis is mediated by T cells having specificity for MBP. Multiple clones of MBP-specific T cells have been isolated from animals suffering from EAE and have been propagated in continuous culture. After in vitro stimulation with MBP, these T cell clones rapidly induce EAE when adoptively transferred to healthy hosts. Importantly, these EAE-inducing T cells are specific not only for the same antigen (MBP), but usually also for a single epitope on that antigen. These observations indicate that discrete populations of autoaggressive T cells are responsible for the pathogenesis of EAE.

Analysis of the TCRs of EAE-inducing T cells has revealed restricted heterogeneity in the structure of these disease-associated receptors. In one analysis of 33 MBP-reactive T cells, only two alpha chain V region gene segments and a single alpha chain J region gene segment were found. Similar restriction of beta chain TCR gene usage was also observed in this T cell population. Only two beta chain V region segments and two J region gene segments were found. More importantly, approximately eighty percent of the T cell clones had identical amino acid sequences across the region of beta chain V-D-J joining. These findings confirm the notion of common TCR structure among T cells with similar antigen specificities and indicate that the TCR is an effective target for immunotherapeutic strategies aimed at eliminating the pathogenesis of EAE.

An alternative mechanism for T cell activation as been suggested in which endogenous and exogenous superantigens have been shown to mediate T-cell stimulation as described, for example, in White et al., *Cell* 56:27–35 (1989) and Janeway, *Cell* 63:659–661 (1990).

The present invention provides an effective method of immunotherapy for psoriasis which avoids many of the problems associated with previously suggested methods of treatment. By administering the peptides of this invention rather than passively administering heterologous antibodies, the host's own immune system is mobilized to suppress the autoaggressive T cells. Thus, the suppression is persistent and may involve any or all immunological mechanisms in effecting that suppression. This multi-faceted response is more effective than the uni-dimensional suppression achieved by passive administration of monoclonal antibodies or ex vivo-derived regulatory T cell clones which requires a highly individualized therapeutic approach because of MHC non-identity among humans in order to avoid graft versus host reactions. The methods of the present invention are also more effective than vaccination with attenuated disease-inducing T cells that lack specificity for the protective antigen on the surface of a particular T cell as well as the variable induction of immunity to that antigen. In addition, vaccination with attenuated T cells is plagued by the same labor intensiveness and need for individualized therapies as noted above for ex vivo derived regulatory T cell clones.

As they relate to psoriasis, the compositions of the present invention comprise TCR fragments from specific T cells that mediate psoriasis. The peptides can be whole TCRs substantially purified from T cell clones, individual T cell receptor chains (for example, alpha, beta, etc.) or portions of such chains, either alone or in combination. The compositions can be homogenous, for example, a single peptide, or can be composed of more than one type of peptide, each of which corresponds to a different portion of the TCR. Further, these peptides can be from different TCRs that contribute to psoriasis. These peptides can be of variable length so long as they can elicit or affect a regulatory response. Preferably, such peptides are between about 5–100 amino acids in length, and more preferably between about 6–25 amino acids in length.

In a further specific embodiment, T cell receptors, whole T cells or fragments of TCRs that contain Vβ3, Vβ13.1 or Vβ17 can be administered to an individual having psoriasis. The effect on the immune system generated in the individual can neutralize or kill T cells having Vβ3, Vβ13.1 or Vβ17 and, thus, prevent or treat the deleterious effects of such Vβ-bearing T cells. Moreover, to the extent that Vβ3, Vβ13.1 or Vβ17 is common to T cell receptors on pathogenic T cells mediating other autoimmune diseases or autoimmune diseases in general, such compositions can also be effective in preventing or reducing the severity of such other autoimmune diseases.

As used herein, "Vβ3" refers to a family of specific human β-chain variable region. Vβ3 has the following amino acid sequence: DVKVTQSSRY LVKRTGEKVF LECVQDMDHE NMFWYRQDPG LGLRLIYFSY DVK-MKEKGDI PEGYSVSREK KERFSLILES AST-NQTSMYL CASS (SEQ ID NO: 1). Kimura, N. et al., *Eur. J. Immunol.* 17:375–383 (1987).

As used herein, "Vβ13.1" refers to a specific human β-chain variable region. Vβ13.1 has the following amino acid sequence NAGVTQTPKF QVLKTGQSMT LQCAQDMNHE YMSWYRQDPG MGLRLIHYSV GAGITDQGEV PNGYNVSRST TEDFPLRLLS AAPSQTSVYF CASS (SEQ ID NO: 2). Li, Y. et al., *J. Exp. Medicine,* 174:1537–1547 (1991).

As used herein, "Vβ17" refers to a specific human β-chain variable region of three T cell receptors. Vβ17 has the following amino acid sequence: DGGITQSPKY LFRKEG-QNVT LSCEQNLNHD AMYWYRQDPG QGLRLIYYSQ IVNDFQKGDI AEGYSVSREK KESFPLTVTS AQKNPTAFYL CASS (SEQ ID NO: 3). Kimura, N. et al., *Eur. J. Immunol.,* 17:375–383 (1987).

The hypervariable or junctional regions are useful for the compositions of the present invention. Hypervariable regions useful in the present invention include CDR1, CDR2, CDR3 and CDR4. The amino acid sequences of the CDR1, CDR2 and CDR4 hypervariable regions for Vβ3, Vβ13.1 and Vβ17 are shown in FIG. 1.

The CDR3, also known as the V(D)J region, is useful as a composition of the present invention since T cell immunity elicited by peptides corresponding to this region is expected to be highly specific for a particular antigen. Due to the recombination of the V, D and J region genes prior to maturation, the amino acid sequence across these regions is virtually unique to each T cell and its clones.

However, as a germ-line element, the CDR2 region is also useful in psoriasis. In psoriasis studies, the results indicate a limited number of Vβs among the activated T cells infiltrating the epidermis. Thus, peptides corresponding to the CDR2 region are viable alternatives for use as compositions of the present invention. For example, the CDR2 region of Vβ3: DPGLGLRLIY FSYDVKMKEK G (fragment of SEQ ID NO: 1), of Vβ13.1: DPGQGLRIY YSQIVNDFQK G (fragment of SEQ ID NO: 2), or of Vβ17: DPGQGLRLIY YSQIVNKFQK G (fragment of SEQ ID NO: 3), can be used.

Modifications in these sequences that do not affect the ability of the receptor or a fragment thereof to act as an immunogen to stimulate the desired effect on the immune system are contemplated and are included in the definition of TCR fragment. The variable region can be joined with any D and J segment of the TCR. Further, representative fragments of Vβ3, Vβ13.1 and Vβ17 are also included in the definition of "Vβ3," "Vβ13.1" and "Vβ17," respectively.

In another embodiment, peptides can correspond to the Vβ regions that contain sequences of high homology which are conserved among pathogenic TCRs. These regions of conserved homology include the conventional CDRs, such as CDR1 and CDR2, which are common to T cells bearing the same Vβ, and also the superantigen binding site, which can be common to pathogenic TCRs bearing different Vβs. The superantigen binding site is also known to be in or around the CDR4 hypervariable region.

The compositions of the present invention comprise peptides of varying lengths corresponding to the TCR or fragments thereof capable of causing an effect on the immune system. The peptides can correspond to regions of the TCR which distinguish that TCR from other nonpathogenic TCRs. Such specific regions can, for example, be located within the various region(s) of the respective TCR polypeptide chains, for example, a short sequence spanning the V(D)J junction, thus restricting the effect on the immune system solely to those T cells bearing this single determinant.

The compositions are administered to an individual exhibiting or at risk of exhibiting psoriasis. Definite clinical diagnosis of psoriasis warrants the administration of the relevant disease-specific TCR compositions. Prophylactic applications are warranted in diseases where the autoimmune mechanisms precede the onset of overt clinical disease. Thus, individuals with familial history of disease and predicted to be at risk by reliable prognostic indicators could be treated prophylactically to interdict autoimmune mechanisms prior to their onset.

TCR peptides can be administered in many possible formulations, including pharmaceutically acceptable media. In the case of a short peptide, the peptide can be conjugated to a carrier, such as KLH, in order to increase its ability to cause an effect on the immune system. The composition can include or be administered in conjunction with an adjuvant, of which several are known to those skilled in the art. After initial immunization with the vaccine, further boosters can be provided. The compositions are administered by conventional methods, in dosages which are sufficient to cause an effect on the immune system. Such dosages can be easily determined by those skilled in the art.

Appropriate peptides to be used for administration can be determined as follows. Disease-inducing T cell clones reactive with the target antigens are isolated from affected individuals. Such T cells are obtained preferably from the site of active autoaggressive activity such as a psoriatic lesion. Alternatively, such T cells can be obtained from blood of affected individuals. The TCR genes from these autoaggressive T cells are then sequenced. Polypeptides corresponding to TCRs or portions thereof that are selectively represented among disease inducing T cells (relative to non-pathogenic T cells) can then be selected as vaccines and made and used as described above. An alternative method for isolating pathogenic T cells is provided by Albertini in PCT Publication No. WO88/10314, published on Dec. 29, 1988.

Alternatively, the compositions can comprise anti-idiotypic antibodies which are internal images of the peptides described above. Methods of making, selecting and administering such anti-idiotype vaccines are well known in the art. See, for example, Eichmann, et al., *CRC Critical Reviews in Immunology* 7:193–227 (1987), which is incorporated herein by reference.

In a further aspect of the present invention, methods of preventing the proliferation of T cells associated with psoriasis are also contemplated. Such methods include determining a T cell receptor binding partner according to the above methods and administering an effective amount of such binding partner in an appropriate form to prevent the proliferation of the T cells. The methods can be used, for example, to build a tolerance to self antigens as in the case of an autoimmune disease.

The present invention also relates to methods of preventing or reducing the severity of psoriasis by inhibiting the binding of a T cell receptor to its TCR binding partner in order to prevent the proliferation of T cells associated with psoriasis. Ligands that are reactive with the T cell receptor or its binding partner at binding sites that inhibit the T cell receptor attachment to the binding partner can be used. Such ligands can be, for example, antibodies having specificity for the T cell receptor or its binding partner.

The invention also provides a method of preventing or reducing the severity of psoriasis in an individual comprising cytotoxically or cytostatically treating Vβ-containing T-cells, particularly Vβ3, Vβ13.1 and Vβ17, in the individual. The Vβ-containing T cells are treated with a cytotoxic or cytostatic agent that selectively binds to the Vβ region of a T cell receptor that mediates psoriasis. The agent can be an antibody attached to a radioactive or chemotherapeutic moiety. Such attachment and effective agents are well known in the art. See, for example, Harlow, E. and Lane, *Antibodies, A Laboratory Manual,* Cold Spring Harbor Laboratory (1988), which is incorporated herein by reference.

As noted, the invention provides the discovery that specific variable regions of the β-chains of three TCRS, designated Vβ3, Vβ13.1, and Vβ17, are closely associated with psoriasis in human subjects. This discovery allows for the detection, prevention and treatment of psoriasis using the methodology set out in this invention.

Specifically, the invention provides a method of diagnosing or predicting susceptibility to psoriasis in an individual comprising detecting T cells having the β-chain variable region from Vβ3, Vβ13.1 or Vβ17 in a sample from the individual, the presence of abnormal levels of such Vβ-containing T cells indicating the pathology or susceptibility to the pathology. The Vβ-containing T cells can be qualitatively or quantitatively compared to that of normal individuals. Such diagnosis can be performed, for example, by detecting a portion of the Vβs that does not occur on non-psoriasis associated β-chain variable region T-cell receptors. The Vβs of the present invention can be detected, for example, by contacting the Vβs with a detectable ligand capable of specifically binding to the individual Vβs. Many such detectable ligands are known in the art, e.g. an enzyme linked antibody. Alternatively, nucleotide probes, complementary to the individual Vβ of interest, encoding nucleic acid sequences can be utilized to detect such Vβ-containing T cells.

The invention also provides a method of preventing or reducing the severity of psoriasis comprising preventing the attachment of a Vβ3-, Vβ13.1- or Vβ17-containing T-cell receptor to its binding partner. In one embodiment, attachment is prevented by binding a ligand to Vβ3, Vβ13.1 or Vβ17. In an alternative embodiment, attachment is prevented by binding a ligand to the Vβ3, Vβ13.1 or Vβ17 binding partner. Attachment can be prevented by known methods, e.g. binding an antibody to the individual Vβs or to its binding partner in order to physically block attachment.

The present invention further relates to a method of preventing or reducing the severity of psoriasis by gene therapy. This method involves the use of vectors having an expression control sequence operatively linked to a nucleic acid molecule encoding a polypeptide. The nucleic acid molecule can be DNA or RNA. The polypeptide can be a TCR or a fragment thereof capable of causing an effect on the immune system, or an anti-idiotype antibody that can be used as a composition in the present invention. Such DNA or RNA can be isolated by standard methods known in the art. The isolated nucleic acid can then be inserted into a suitable vector by known methods. An expression control sequence is operatively linked to a nucleic acid molecule when it directs the transcription and translation of that molecule in an appropriate host cell. This includes provision of appropriate start and stop codons. Expression vectors and their use are well known to the art. Such methods are described, for example, in Sambrook et al., *Molecular Cloning—A Laboratory Manual*, Cold Spring Harbor Laboratory, Cold Spring Harbor, N.Y., (1989) which is incorporated herein by reference.

The vector is subsequently administered directly into a tissue of an individual. Preferably, the DNA or RNA-containing vector is injected into the skeletal muscle of the individual. For example, a 1.5 cm incision can be made to expose the quadricep muscles of the subject. A 0.1 ml solution containing from 10–100 µg of a DNA or RNA plasmid and 5–20% sucrose is injected over 1 minute into the exposed quadricep muscles about 0.2 cm deep. The skin is thereafter closed. The amount of DNA or RNA vector can range from 10 to 100 µl of hypotonic, isotonic or hypertonic sucrose solutions or sucrose solutions containing 2 mM $CaCl_3$. The plasmid containing solutions can also be administered over a longer period of time, for example, 20 minutes, by infusion. The in vivo expression of the desired gene can be tested by determining an increased production of the encoded polypeptide by the subject according to methods known in the art or as described, for example, in Wolff et al., *Science* 247:1465–1468 (1990).

It is believed that the treated cells will respond to the direct injection of DNA or RNA by expressing the encoded polypeptide for at least about 60 days. Thus, the desired TCR, fragment capable of causing an effect on the immune system or anti-idiotype antibody can be effectively expressed by the cells of the individual as an alternative to vaccinating with such polypeptides.

The present invention also relates to vectors useful in the gene therapy methods and can be prepared by methods known in the art. Compositions containing such vectors and a pharmaceutically acceptable medium are also provided. The pharmaceutically acceptable medium should not contain elements that would degrade the desired nucleic acids.

The following example is intended to illustrate but not limit the invention.

EXAMPLE

Preferential Usage of Vβ3, Vβ13.1 and V17 in Psoriasis

All psoriasis patients for this study were enrolled at the-Psoriasis Research Institute (Palo Alto, Calif.). The clinical background information is provided in Table I. None of the patients were treated by any topical medications for at least two weeks before sampling. Epidermal shavings measuring 0.4 mm thickness by 6 $cm^2$ were taken from a clinically active lesion from back, arm or abdomen using a Castroviejo keratotome (Storz Instruments Inc., St. Louis, Mo.) Samples were shipped overnight in RPMI containing 1% human AB serum at 4° C.

Skin samples were cut with a scalpel and treated with No-zyme cell dissociation buffer (GIBCO BRL, Gaithersburg, Md.) with 0.1% DNase for 15 minutes at 37° C. Undigested pieces were further treated with 0.25% trypsin with 0.1% DNase for 10 minutes. Cells released were spun down, resuspended in ice-cold PBS (with DNase) to lyse keratinocytes (Foster C. A. et al., *J. Exp. Med.*, 171:997–1013 (1990)). Further enrichment of lymphocytes was done by collecting interface cells after separating on Ficoll-Hypague gradient. Peripheral blood leukocytes (PBLs) were isolated by Ficoll Hypague as suggested by the manufacturers.

Lymphocyte enriched population was stained with monoclonal mouse anti-human CD4, CD8, CD25 antibodies and sorted on FACStar Plus (Becton-Dickinson, Mountain View, Calif.). Cytochrome conjugated normal mouse immunoglobulins were used as control antibodies to set the gates. $CD8^+$ (or $CD8^+CD25^+$), $CD4^+$ (or $CD4^+CD25^+$) cells were collected, spun down and to the pellet RNazol was added, samples vortexed and then frozen at -70° C.

Total RNA was isolated using RNazol B (Biotecx Laboratories, Inc., Houston, Tex.) according to the manufacture's directions. Twenty micrograms (µg) of glycogen (Boehringer Mannheim, Indianapolis, Ind.) was added to coprecipitate the RNA. Mock RNA tubes containing no nucleic acids were simultaneously processed to ensure there was no reagent contamination. RNA was collected after overnight precipitation at -20° C. by centrifugation at 14,000 rpm for 25 minutes, followed by a 75% ethanol wash. After aspirating all ethanol, the air-dried RNA pellet was resuspended in DEPC-water and taken for cDNA synthesis. cDNA synthesis was performed in a 10 µl volume using an antisense CB primer, GCGGCTGCT CAG-GCAGTA (SEQ ID NO: 4), which binds approximately 220 nucleotides downstream from the Jβ) at a final concentration of 100 nM. The Superscript Preamplification System was used for all cDNA syntheses as suggested by the manufacturer (BRL, Gaithersburg, Md.). Since such small. amounts of RNA cannot be quantitated by absorbance at 260 nm, blood lymphocyte RNA sample was equilibrated to contain the same amount of cell-equivalent's worth of total RNA as that in skin in order to compare the relative signals obtained in the PCR. In addition, RNA extraction and further analysis was performed on only samples that contained at least 1000 sorted cells.

PCR amplifications of cDNA for the skin and blood samples were prepared and run simultaneously in the same block using a Perkin Elmer Cetus Thermal cycler (Perkin Elmer Cetus, Norwalk, Conn.). "Water blank" controls were included to run through the PCR and all previous protocols to ensure no contamination. The thermal cycling profiles were as follows: One time at 94° C. for 5 minutes to denature all RNA:DNA hybrids, followed by cyclings of 94° C. for 1 minute, 55° C. for 1 minute, and 72° C. for 1 minute. Number of cycles (mean=33) varied depending on the amount of input template. Hot start PCR was employed to minimize spurious priming by using AmpliWax gems (Perkin Elmer Cetus).

Twenty-two individual PCR reactions were set up in 50 µl in GeneAmp tubes (Perkin Elmer Cetus) with each tube containing the appropriate Vβ-specific primer. Most sense primers were taken from Choi, Y., et al., *Proc. Natl. Acad. Sci. USA.*, 86:8941–8945 (1989) or Wucherpfeennig, K. W., et al., *Science*, 248:1016–1019 (1990) (Vβs 1, 11, 15, and 19) which are incorporated herein by reference although a few others were changed as follows (5'–3'): Vβ6-TCAGGTGTGA TCCAATTTC (SEQ ID NO: 5); Vβ8-TCTGGTACAG ACAGACCATG AT (SEQ ID NO: 6); Vβ12-GATACTGACA AAGGAGAAGT CTCAGAT (SEQ ID NO: 7); Vβ17-TCACAGATAG TAAATGACTT TCAG (SEQ ID NO: 8). These primers were changed from those previously published in order to capture all subfamily members (i.e., Vβ6, 8) or to prevent cross-priming onto closely related subfamilies' members (Vβ12 and 13 are closely related). All 22 primers have been extensively tested by sequencing to ensure that they are specific for only the desired/predicted subfamily. At the 3'-end, a $^{33}$P-γATP end labeled antisense Cβ (TTGGGTGTGG GAGATCTCTG C (SEQ ID NO: 9), which primes approximately 55 nucleotides from the Jβ) was used.

Upon completion of the PCR reaction, 15 µl of each PCR reaction was run on a 6% non-denaturing polyacrylamide gel to resolve the[]specific PCR products. The radioactivity of each PCR product was then directly scanned from each dried gel using an Ambis Radioanalytic System (Ambix, San Diego, Calif.). The total cpms of all Vβ PCR products on each gel was summed and divided into each individual cpm value to establish a value for each Vβ expressed as a percentage. Both skin and blood samples were treated as identically as possible (equilibrated templates, identical cycling conditions, and equivalent cycle number in many instances). A relative comparison between the percentage of each Vβ in the skin to that in the blood was made throughout this study.

To sequence the Vβ PCR products, PUC18 plasmid was used and dideoxy cycle sequencing was performed as suggested by the manufacturers (Applied Biosystems Inc., Foster City, Calif.) using the ABI 373 Sequencer (Applied Biosystems, Foster City, Calif.). Each sequence obtained was scanned against the panel of known human Vβ and Jβ genes to establish identity using PC Gene (Intelligenetics, Mountainview, Calif.). Each nucleotide sequence was translated and reported as the predicted amino acid sequence.

To examine if there is a preferential usage of a certain Vβ gene in psoriatic plaque lesion, we isolated CD8$^+$ T cells from both the psoriatic epidermis and the PBL, and the percent of expression of Vβ1 to Vβ20 was determined as described above. It is reasoned that T cells which are involved in plaque formation should be stimulated in situ by antigen or superantigen on the skin elements. Therefore, one criteria for preferential usage of a Vβ in the skin was that it had to represent at least 10% of the total Vβs in the skin and its relative expression of skin to PBL levels was at least 2. We also included Vβs of which the expression was very high (greater than 30%) in the skin, although the relative expression of skin to PBL level was less than 2 as a result of an unusually high expression in the PBL. These Vβs were included since otherwise an active systemic response to superantigens, relevant or irrelevant to psoriasis, would mask the significance of a highly expressed Vβ in the skin.

As shown in Table II, among the seven patients for which TCR Vβ analysis of skin and PBL were performed, five had a preferential expression of Vβ13.1 gene in the skin, and among these five patients, three also preferentially used Vβ3. The two patients that did not show a preferential expression of Vβ13.1 and Vβ3, a common usage of Vβ17 was detected. It should be noted here, CD8$^+$CD25$^+$ T cells were studied in some patients and CD8$^+$ T cells were studied in others when samples showed a low number of double positive cells (on FACS screen) and a decision was made to sort all CD8$^+$ T cells in order to obtain enough cells (at least 1000) to study.

To determine if these TcR Vβ-bearing cells persisted in these chronic plaques, four out of five of the patients that used Vβ13.1 (with or without Vβ3) were sampled for the second time. The second sample was taken either from the original lesion or at a different site (see Table I), a different amount of time elapsed between the first and second sampling for different patients. The results of these repeat patients are given in Table III. As shown, patient #5019, which used Vβ13.1 (Table II) in the first sampling, was again shown to use Vβ13.1. Patients #5022 and #5026, which preferentially used Vβ3 and Vβ13.1, were also again shown to use these two Vβs. Patient #5029, which used Vβ3 and Vβ13.1, upon the second shaving, retained the Vβ3 usage. The Vβ13.1 for #5029, according to the criteria that we set, was not preferentially used; nevertheless, the absolute percent of expression was still above 10%. It is noted here that among the repeat samples, two were-from the original lesion (#5026, #5029), two were from different sites (#5019, #5022). Therefore, these data not only suggest the persistence of these Vβs in the lesion, but also their common presence at different sites.

Analysis of CD8$^+$CD25$^+$ T cells isolated from two atopic dermatitis as shown in Table IV, does not demonstrate an elevated Vβ3 or Vβ13.1 expression in the skin compared to that of PBL. Therefore, repeat findings of elevated level of Vβ3 and Vβ13.1 TCR genes in psoriatic lesions, and the absence of such findings in atopic dermatitis patients, both indicate an in situ expansion of these T cells to either skin antigens or superantigens in the psoriatic plaques.

To address the question if antigens or superantigens were seen in the skin by these T cells, we analyzed their clarity by sequencing the V-D-J junctions. As shown in Table V, monoclonality (or nearly) of Vβ13.1-bearing CD8$^+$ T cells in the skin was observed in patients #5019 and #5022, a marked oligoclonality was seen in patients #5026 and #5029. Vβ13.1 sequences found in PBL were much more polyclonal. These results, therefore, strongly suggest the involvement of limited numbers of antigenic epitopes rather than superantigens in the stimulation of Vβ13.1-bearing CD8⁺ T cells in these lesions. Vβ3 sequences in the skin, except in patient #5029 where a nearly monoclonality was observed, were less oligoclonal than Vβ13.1 sequences. However, skin antigen rather than superantigen still seems to be responsible for the in situ expansion of Vβ3-bearing CD8⁺ T cells since superantigen would have also stimulated Vβ-bearing CD4⁺ T cells, (Kotzin, B. L. et al., *Proc. Natl. Acad. Sci. (USA)*, 88:9161–9165 (1991); Miethke T., et al., *Int. J. Med. Microbiol.*, 275:264–268 (1991)) in the skin, in contrast to our finding, as shown in Table VI. As for Vβ13.1 CD4⁺ T cells in the skin, in the two patients that had a lesser (as compared to CD8⁺ T cells) elevation over the PBL, sequence analysis (Table V) showed much diverse junctional sequences than that of Vβ13.1-bearing CD8⁺ T cells.

Stimulation of Vβ3 and Vβ13.1 CD8⁺ T cells by antigen in the skin is further supported by sequence data obtained from repeated patients. As shown in Table VII, in two (#5022, #5029) out of three repeat patients that we had obtained sequences of the V-D-J junction, same sequences were obtained, either in the repeat shave of the same lesion (patient #5029) or of a different site. Persistence of T cells with the same antigenic specificity (same V-D-J sequence) in a lesion and the presence of them in different lesions, both reflected an antigenic selection in the skin.

TABLE I

Clinical History of Psoriasis Patients

| Patient (Repeat of) | M/F | AGE | Duration of Psoriasis | Extent of Psoriasis | Site of Shave | Score of Lesion | Notes |
|---|---|---|---|---|---|---|---|
| #5019 | M | 40 | 24 | 30% | back | 9 | — |
| #5045 (#5019) | | | | 10% | right arm | 7 | Repeat was done 8 months later, patient improved |
| #5022 | M | 50 | 35 | 40% | back | 4 | — |
| #5041 (#5022) | | | | 40% | right arm | 5 | Repeat was 7 months later |
| #5026 | M | 38 | 10 | 20% | back | 5 | — |
| #5043 (#5026) | | | | 20% | back (same lesion) | 5 | Repeat was 5 months later |
| #5029 | F | 24 | 8 | 25% | arm | 5 | — |
| #5039 (#5029) | | | | 25% | arm (same lesion) | 6 | Repeat was 3.5 months later |
| #5046 | F | 43 | 30 | 40% | abdomen | 5 | — |
| #5025 | M | 36 | 4 | 10% | back | 8 | — |
| #5025 | M | 38 | 20 | 10% | back | 7 | — |

TABLE II

Percentage of Vβ Gene Expression in skin and PBL CD8⁺ cells from Psoriasis Patients

| Patient | #5019 | | #5022 | | #5026 | | #5029 | | #5046 | | #5025 | | #5028 | |
| Cells Isolated | CD8⁺CD25⁺ | | CD8⁺ | | CD8⁺ | | CD8⁺CD25⁺ | | CD8⁺ | | CD8⁺ | | CD8⁺CD25⁺ | |
| Vβ/Tissue | Skin | PBL | Skin | PBL | Skin | PBL | Skin | PBL | Skin | PBL | Skin | PBL | Skin | PBL |
|---|---|---|---|---|---|---|---|---|---|---|---|---|---|---|
| 1 | 2.5 | 3.9 | — | 1.2 | 1.5 | 2.5 | 0.7 | 1.4 | — | — | 0.3 | 3.3 | 2.3 | 0.7 |
| 2 | 3.3 | 12.2 | 2.0 | 3.7 | 7.1 | 4.6 | 20.5 | 11.6 | — | 18.5 | 16.3* | 6.6 | 3.4 | 14.6 |
| 3 | 2.1 | 3.7 | 43.0* | 14.0 | 26.5* | 7.3 | 15.5* | 5.0 | — | 17.1 | 7.5 | 16.3 | 9.3 | 25.8 |
| 4 | 1.7 | 4.3 | — | 0.1 | 0.2 | 1.2 | 0.5 | 3.4 | 1.4 | 4.7 | 2.1 | 3.2 | — | 1.6 |
| 5.1 | 0.2 | 0.9 | — | — | 0.3 | 1.0 | 0.3 | 0.7 | — | 4.7 | 0.7 | 1.1 | 0.3 | — |
| 5.2 | 0.2 | 1.0 | — | — | 0.2 | 0.6 | 0.3 | — | — | — | 0.6 | 1.8 | — | — |
| 6 | 14.8 | 11.1 | 6.7 | 11.0 | 16.0 | 18.6 | 6.2 | 12.5 | 61.9* | 17.4 | 10.4 | 12.2 | 0.3 | 9.3 |
| 7 | 2.7 | 10.8 | 8.6 | 18.6 | 16.3* | 7.8 | 7.2 | 8.2 | — | 22.2 | 6.7 | 10.2 | 15.6* | 6.7 |
| 8 | 6.7 | 7.2 | 1.6 | 2.2 | 5.2 | 11.7 | 9.8 | 7.6 | 3.0 | 2.9 | 3.1 | 5.2 | 0.8 | 4.9 |
| 9 | 0.3 | 1.3 | — | — | — | 0.5 | 0.9 | 1.5 | — | — | 0.4 | 2.9 | — | 1.4 |
| 10 | 0.2 | 1.3 | — | 0.5 | — | 0.6 | 0.2 | — | — | 3.6 | — | 0.5 | — | 0.2 |
| 11 | 0.3 | 1.5 | 0.4 | 1.2 | 1.4 | 0.5 | 0.3 | 0.5 | — | — | 0.8 | — | — | 1.9 |
| 12 | 0.7 | 1.7 | 0.2 | 0.4 | — | 0.3 | 0.9 | 1.0 | — | — | 0.4 | 1.2 | — | 1.1 |
| 13.1 | 59.6* | 14.4 | 32.5* | 28.5 | 13.5* | 6.5 | 16.1* | 5.3 | 25.0* | — | 2.9 | 11.5 | 0.2 | 6.0 |
| 13.2 | 1.6 | 1.7 | 2.2 | 10.3 | 0.8 | 5.7 | 14.7 | 10.9 | — | 2.2 | 1.6 | 6.0 | 0.5 | 0.9 |
| 14 | 0.9 | 1.1 | — | — | 3.3 | 0.7 | 0.3 | — | — | — | 3.3 | 1.9 | 2.5 | 1.0 |
| 15 | 0.2 | 1.8 | — | — | — | 4.4 | 1.4 | 1.4 | — | 1.0 | 4.4 | 0.6 | 4.3 | 4.5 |
| 16 | 0.2 | 2.4 | 0.8 | 2.3 | — | 9.5 | 0.2 | 4.9 | 8.7 | 4.4 | 0.7 | 0.6 | 0.6 | 4.0 |
| 17 | 1.0 | 13.0 | 1.7 | 1.7 | 5.9 | 13.8 | 1.8 | 11.8 | — | — | 29.1* | 9.8 | 35.6* | 10.8 |
| 18 | 0.4 | 1.4 | — | 1.5 | — | 1.2 | 0.8 | 3.5 | — | — | 7.1 | 3.2 | 1.1 | 2.8 |
| 19 | — | 1.2 | — | — | 1.6 | 0.2 | 1.3 | 2.9 | — | 0.2 | — | 1.3 | — | — |
| 20 | 1.0 | 2.6 | 0.6 | 2.8 | — | 0.7 | 0.5 | 5.8 | — | 1.1 | 1.6 | 0.7 | 23.2* | 1.9 |

*Vβs of which the % expression in skin is above 10 and is at least 2× of that in PBL, of Vβs of which the % expression is equal to or above 30.

TABLE III

TcR Vβ Gene Expression in Skin and PBL CD8+ T Cells of Psoriasis Repeat Patients

| Patient Cells Isolated | #5039 (#5029) CD*+ | | #5041 (#5022) CD8+CD25+ | | #5043 (#5026) CD8+ | | #5045 (#5019) CD8+CD25+ | |
|---|---|---|---|---|---|---|---|---|
| Vβ/Tissue | Skin | PBL | Skin | PBL | Skin | PBL | Skin | PBL |
| 1 | 0.1 | 0.7 | — | — | — | — | 0.2 | — |
| 2 | 17.1 | 15.9 | — | 8.3 | 2.3 | 7.4 | — | 2.7 |
| 3 | 21.1* | 5.9 | 74.6* | 49.7 | 15.8* | 7.6 | — | — |
| 4 | 0.4 | — | — | — | — | — | — | 0.6 |
| 5.1 | — | 2.1 | 1.0 | 1.3 | — | — | — | 3.2 |
| 5.2 | — | — | 0.2 | — | — | — | — | — |
| 6 | 6.4 | 7.3 | 3.5 | — | 13.9 | 24.2 | 11.0 | 27.1 |
| 7 | 3.4 | 14.0 | — | — | — | 1.0 | 7.1 | — |
| 8 | 13.8* | 6.3 | — | 4.7 | 4.0 | 4.3 | 3.2 | 2.3 |
| 9 | 1.1 | — | — | 6.9 | 4.0 | 3.1 | 4.1 | 11.5 |
| 10 | — | 0.8 | — | 10.0 | — | — | — | — |
| 11 | 2.1 | 2.8 | — | 10.4 | — | — | — | 5.9 |
| 12 | — | — | — | — | — | — | — | — |
| 13.1 | 11.1 | 8.3 | 12.3* | — | 37.5* | 12.3 | 74.4* | 19.8 |
| 13.2 | 10.3 | 9.3 | 8.2 | — | 19.3 | 22.7 | — | 22.3 |
| 14 | — | — | — | 0.4 | — | — | — | — |
| 15 | 0.6 | 2.7 | — | 8.3 | 3.2 | 4.6 | — | — |
| 16 | 1.3 | 3.4 | — | — | — | 12.9 | — | 1.8 |
| 17 | — | 4.0 | 0.2 | — | — | 0.2 | — | 1.9 |
| 18 | 5.1 | 5.9 | — | — | — | — | — | 0.9 |
| 19 | 6.1 | 5.2 | — | — | — | — | — | — |
| 20 | — | 5.5 | — | — | — | — | — | — |

*see Table II

TABLE IV

TcR Vβ Gene Usage by Skin and PBL CD8+T Cells From Atopic Dermatitis Patients

| Patient Cells Isolated | #5034 CD8+CD25+ | | #5035 CD8+CD25+ | |
|---|---|---|---|---|
| Vβ/Tissue | Skin | PBL | Skin | PBL |
| 1 | 1.9 | — | 1.6 | — |
| 2 | 15.6 | 26.4 | 11.4 | 6.9 |
| 3 | 5.6 | 24.8 | 16.1 | 44.6 |
| 4 | 0.3 | 4.4 | 4.9 | 2.2 |
| 5.1 | 1.1 | 0.1 | 0.6 | — |
| 5.2 | — | — | — | — |
| 6 | 10.2 | 6.5 | 17.6 | 9.2 |
| 7 | 27.6* | 19.4 | 10.1 | 5.5 |
| 8 | 5.6 | 2.6 | — | 3.8 |
| 9 | — | 1.2 | — | 0.6 |
| 10 | — | — | 6.0 | 0.3 |
| 11 | 2.7 | — | — | — |
| 12 | — | — | 2.0 | 0.8 |
| 13.1 | 4.1 | 3.5 | 8.8 | 8.2 |
| 13.2 | 2.1 | 6.8 | — | 3.5 |
| 14 | — | 0.4 | — | — |
| 15 | 0.5 | — | — | 0.9 |
| 16 | 1.9 | 0.5 | — | 3.9 |
| 17 | 1.3 | 1.5 | 2.9 | 6.1 |
| 18 | 5.1 | — | 17.9* | 0.6 |
| 19 | 2.0 | — | — | 1.2 |
| 20 | 12.4 | 1.9 | — | 1.9 |

*See Table II

TABLE V

Analysis of β-Chain Sequences on CD8+ T Cells from Psoriatic Lesions and PBL

| PATIENT # | TISSUE | CELLS | Vβ | % OF TOTAL Vβ* | FREQUENCY OF CLONES | JUNCTIONAL SEQUENCES (V-D-J) | NOTES |
|---|---|---|---|---|---|---|---|
| #5019 | Skin | CD8+CD25+ | 13.1 | 59.6 | 25ª/26 | ªCA TREVAGLSV TDTQ (2.3) (SEQ ID NO: 10) | None is the same |
| | PBL | CD8+CD25+ | 13.1 | 14.4 | 4/21, 3/21, | | |

TABLE V-continued

Analysis of β-Chain Sequences on CD8+ T Cells from Psoriatic Lesions and PBL

| PATIENT # | TISSUE | CELLS | Vβ | % OF TOTAL Vβ* | FREQUENCY OF CLONES | JUNCTIONAL SEQUENCES (V-D-J) | NOTES |
|---|---|---|---|---|---|---|---|
| | Skin | CD8+CD25+ | 6 | 14.8 | 2/21 1/21 for the rest 6/21, 5/21, 2/21 1/21 for the rest | | sequence as that found in the skin |
| #5022 | Skin | CD8+ | 13.1 | 32.5 | 28ª/28 | ªCASS YSSVL NTEA (1.1) (SEQ ID NO: 11) | None is the same as that found in the skin |
| | PBL | CD8+ | 13.1 | 28.5 | 5/25, 3/25, 2/25, 2/25, 2/25 1/25 for the rest | | |
| | Skin | CD8+ | 3 | 43.0 | 7ª/20 5ᵇ/20 5ᶜ/20 2/20, 1/20 | ªCASS LNSL NTEA (1.1) (SEQ ID NO: 12) ᵇCASA PYQDST YEQY (2.7) (SEQ ID NO: 13) ᶜCASS PHVLAGASGG YNEQ (2.1) (SEQ ID NO: 14) | |
| #5026 | Skin | CD8+ | 13.1 | 13.5 | 6ª/14 6ᵇ/14 1/14, 1/14 | ªCASS PLGV GNTIY (1.3) (SEQ ID NO: 15) ᵇCASS YSTGG NEQF (2.1) (SEQ ID NO: 16) | |
| | Skin | CD8+ | 3 | 26.5 | 3ª/8 2ᵇ/8 2ᶜ/8 1ᵈ/8 | ªCASL GVM NTEA (1.1) (SEQ ID NO: 17) ᵇCASS SLPRFGQD TGEL (2.2) (SEQ ID NO: 18) | |
| | Skin | CD4+ | 13.1 | 15.1 | 2/8, 2/8 1/8 for the rest | ᶜCASS LEGI NIQY (2.4) (SEQ ID NO: 19) ᵈCATN TEG SYEQ (2.7) (SEQ ID NO: 20) | |
| #5029 | Skin | CD8+CD25+ | 13.1 | 16.1 | 10ª/17 5ᵇ/17 1/17 for the rest | ªCASS PNRVS SYNE (2.1) (SEQ ID NO: 21) ᵇCASS YRAGGL DTQY (2.3) (SEQ ID NO: 22) | |
| | PBL | CD8+CD25+ | 13.1 | 5.3 | 2/13, 2/13 1/13 for the rest | | None is the same as sequences found in skin |
| | Skin | CD4+CD25+ | 13.1 | 13.8 | 6/22, 4/22, 3/22, 2/22 1/22 for the rest | | |
| | Skin | CD8+CD25+ | 3 | 15.5 | 25ª/28 3ᵇ/28 | ªCASS VPGPT NTEAF (1.1) (SEQ ID NO: 23) ᵇCAS GTGLTSP GELF (2.2) (SEQ ID NO: 24) | |
| | PBL | CD8+CD25+ | 3 | 5 | 2/7 ª1/7 for the rest | | |
| | Skin | CD8+CD25+ | 6 | 6.2 | 4/22, 4/22, 4/22, 2/22 1/22 for the rest | a among which one is CASS VPGPT NTEAF (1.1) (SEQ ID NO: 23) | |
| #5025 | Skin | CD8+ | 17 | 29.1 | 12ª/12 | ªCASS INTRASGRHY EQF (2.1) (SEQ ID NO: 25) | |

TABLE V-continued

Analysis of β-Chain Sequences on CD8+ T Cells from Psoriatic Lesions and PBL

| PATIENT # | TISSUE | CELLS | Vβ | % OF TOTAL Vβ* | FREQUENCY OF CLONES | JUNCTIONAL SEQUENCES (V-D-J) | NOTES |
|---|---|---|---|---|---|---|---|
| #5028 | Skin | CD8+CD25+ | 17 | 35.6 | 9a/12 | aCASS IPGRG YGYT (1.2) (SEQ ID NO: 26) | |
| | | | | | 3b/12 | bCASR PGGGPATIA NEQF (2.1) (SEQ ID NO: 27) | | aRadioactivity of the PCR product of a specific Vβ divided by radioactivity of all Vβ products from a given sample.

TABLE VII

Analysis of β-Chain Sequences on CD8+ T Cells from Skins of Repeat Psoriasis Patients

| PATIENT # | REPEAT OF | ANALYTICAL SITE | CELLS | Vβ | % of TOTAL Vβ* | FREQUENCY of CLONES | JUNCTIONAL SEQUENCES | Notes Found in 1st Sample | Frequency in 1st Sample |
|---|---|---|---|---|---|---|---|---|---|
| #5039 | #5029 | same | CD8+ | 13.1 | 13.8 | 15a/15 | aCASS PNRVS SYNE (2.1) (SEQ ID NO: 21) | Yes | 10/17 |
| | | | | 3 | 21.1 | 7a/10 | aCASS VPGPT NTEAF (1.1) (SEQ ID NO: 23) | Yes | 25/28 |
| | | | | | | 1b/10 | bCAS GTGLSP GELF (2.2) (SEQ ID NO: 24) | Yes | 3/28 |
| | | | | | | 1/10 for rest | | | |
| #5041 | #5022 | different | CD8+CD25+ | 13.1 | 12.3 | 9a/14 | aCASS YSSVL NTEA (1.1) (SEQ ID NO: 11) | Yes | 28/28 |
| | | | | | | 3b/14 | bCASR ELGQIFGV EKLF (1.4) (SEQ ID NO: 28) | No | |
| | | | | | | 1/14 for rest | | | |
| | | | | | | | | Yes | 5/20 |
| | | | | 3 | 74.6 | 9a/12 | aCAS APYQDST YEQY (2.7) (SEQ ID NO: 13) | Yes | 7/20 |
| | | | | | | 3b/12 | bCASS LNSL NTEA (1.1) (SEQ ID NO: 12) | | |
| #5043 | #5026 | same | CD8+ | 13.1 | 37.5 | 4a/12 | aCASS QSGGNYR EQYF (2.7) (SEQ ID NO: 29) | No | |
| | | | | | | 4b/12 | bCASS RTLGW EQYF (2.7) (SEQ ID NO: 30) | No | |
| | | | | | | 3c/12 | cCASS EDGGLG TEAF (1.1) (SEQ ID NO: 31) | No | |
| | | | | | | 2d/12 | dCA TLAGTGMRN EQYF (2.7) (SEQ ID NO: 32) | No | |
| | | | | | | | | No | |
| | | | | | | | | No | |
| | | | | 3 | 15.8 | 8a/14 | aCASS LTPSGG SYEQ (2.7) (SEQ ID NO: 33) | | |
| | | | | | | 6b/14 | bCAS LGVL NTEA (1.1) (SEQ ID NO: 34) | | |

*See Table V

TABLE VI

Expression of TcR Genes by CD4+ T Cells in Skin and PBL of Psoriasis Patients

| Patient Cells Isolated | #5020 CD4+CD25+ | | #5021 CD4+ | | #5026 CD4+ | | #5029 CD4+CD25+ | | Patient Cells Isolated | #5020 CD4+CD25+ | | #5021 CD4+ | | #5026 CD4+ | | #5029 CD4+CD25+ | |
|---|---|---|---|---|---|---|---|---|---|---|---|---|---|---|---|---|---|
| Vβ/Tissue | Skin | PBL | Skin | PBL | Skin | PBL | Skin | PBL | Vβ/Tissue | Skin | PBL | Skin | PBL | Skin | PBL | Skin | PBL |
| 1 | 3.0 | 1.5 | 3.0 | 1.8 | 2.6 | 2.4 | 0.5 | 0.9 | 12 | 0.1 | 1.5 | 0.3 | 0.7 | 0.7 | 0.8 | 0.8 | 1.4 |
| 2 | 8.0 | 16.6 | 5.4 | 15.1 | 31.5* | 24.2 | 34.1* | 23.4 | 13.1 | 5.5 | 9.5 | 13.5 | 14.2 | 15.1 | 7.8 | 13.8 | 9.2 |
| 3 | 8.1 | 9.7 | — | 3.9 | — | 8.7 | 5.2 | 2.5 | 13.2 | 3.4 | 3.3 | 7.3 | 7.7 | 4.8 | 4.6 | 5.3 | 8.5 |
| 4 | 4.4 | 4.9 | 0.3 | 1.6 | 0.7 | 2.6 | 0.9 | 2.2 | 14 | 2.9 | 0.6 | 0.4 | 0.1 | — | 0.3 | 0.4 | — |
| 5.1 | — | 1.8 | 0.1 | 1.1 | 1.8 | 3.2 | 1.2 | 0.9 | 15 | — | 1.7 | 0.6 | 0.9 | 2.4 | 1.8 | 1.2 | 1.6 |
| 5.2 | 1.2 | 0.9 | 0.3 | 0.1 | 1.1 | 0.9 | 1.0 | — | 16 | — | 3.1 | 0.4 | 2.4 | 0.9 | 0.5 | 1.4 | 2.5 |
| 6 | 17.8 | 13.9 | 8.8 | 15.9 | 8.9 | 15.0 | 5.4 | 13.6 | 17 | 3.3 | 7.0 | 1.8 | 4.8 | 8.2 | 3.2 | 3.6 | 6.4 |
| 7 | 19.9* | 6.1 | 1.8 | 7.0 | 3.0 | 6.1 | 4.8 | 6.9 | 18 | 1.1 | 3.3 | 7.8 | 10.6 | 5.8 | 6.0 | 4.9 | 9.3 |
| 8 | 14.7* | 5.5 | 46.1* | 7.3 | 7.2 | 5.0 | 4.3 | 5.4 | 19 | — | 0.3 | — | 0.6 | 0.3 | 0.5 | 0.2 | 0.3 |
| 9 | — | 3.6 | 1.5 | 0.6 | 0.8 | 1.7 | 1.2 | 1.0 | 20 | 6.7 | 2.0 | 0.3 | 1.7 | 2.6 | 1.2 | 7.9 | 2.6 |
| 10 | — | 0.5 | 0.3 | 0.6 | 0.6 | 1.3 | — | — | | | | | | | | | |
| 11 | — | 2.6 | 0.3 | 1.2 | 1.2 | 2.1 | 2.5 | 1.5 | | | | | | | | | |

*See Table II

Although the invention has been described with reference to the presently-preferred embodiments, it should be understood that various modifications can be made without departing from the spirit of the invention. Accordingly, the intention is limited only by the claims that follow.

We claim:

1. A method of suppressing activity of T cells expressing Vβ3, Vβ13.1 or Vβ17 T cell receptors in a human individual having psoriasis, comprising administering to said individual an effective amount of an immunogenic peptide comprising the amino acid sequence of a peptide fragment of a non-constant region of a human Vβ3, Vβ13.1 or Vβ17 T cell receptor chain, wherein said peptide fragment is identical in amino acid sequence to the amino acid sequence of a human Vβ3, Vβ13.1 or Vβ17 T cell receptor chain.

2. The method of claim 1, wherein said non-constant region is the CDR1, CDR2 or CDR4 region of said T cell receptor chain.

3. The method of claim 2, wherein said non-constant region is the Vβ3 CDR2 region comprising the sequence DPGLGLRLIY FSYDVKMKEK G (amino acids 38–58 of SEQ ID NO: 1).

4. The method of claim 2, wherein said non-constant region is the Vβ13.1 CDR2 region comprising the sequence DPGMGLRLIH YSVGAGITDQ G (amino acids 38–58 of SEQ ID NO: 2).

5. The method of claim 2, wherein said non-constant region is the Vβ17 CDR2 region comprising the sequence DPGQGLRLIY YSQIVNDFQK G (amino acids 38–58 of SEQ ID NO: 3).

6. The method of claim 1, wherein said non-constant region is the CDR3 region of said T cell receptor chain.

7. The method of claim 1, wherein said immunogenic peptide is administered more than once.

8. A pharmaceutical composition for suppressing activity of T cells expressing Vβ13.1 and Vβ3 T cell receptors in a human individual having psoriasis, comprising a pharmaceutically acceptable medium, an effective amount of an immunogenic peptide comprising the amino acid sequence of a first peptide fragment of a non-constant region of a human Vβ13.1 T cell receptor chain, and an effective amount of an immunogenic peptide comprising the amino acid sequence of a second peptide fragment of a non-constant region of a human Vβ3 T cell receptor chain, wherein said first peptide fragment is identical in amino acid sequence to the amino acid sequence of a human Vβ13.1 T cell receptor chain and said second peptide fragment is identical in amino acid sequence to the amino acid sequence of a human Vβ3 cell receptor chain.

9. The pharmaceutical composition of claim 8, wherein said non-constant regions are the CDR1, CDR2 or CDR4 regions of said T cell receptor chains.

10. The pharmaceutical composition of claim 8, wherein said non-constant regions are the Vβ13.1 CDR2 region comprising the sequence DPGMGLRLIH YSVGAGITDQ G (amino acids 38–58 of SEQ ID NO: 2) and the Vβ3 CDR2 region comprising the sequence DPGLGLRLIY FSYDVKMKEK G (amino acids 38–58 of SEQ ID NO: 1).

11. The pharmaceutical composition of claim 8, wherein said pharmaceutically acceptable medium comprises an adjuvant.

12. A method of suppressing proliferation of Vβ3-, Vβ13.1- or Vβ17-expressing T cells in a human individual having psoriasis, comprising administering to said individual an effective amount of a cytotoxic or cytostatic agent, wherein said agent comprises an antibody, and wherein said antibody selectively binds Vβ3, Vβ13.1 or Vβ17 expressed by said T cells.

13. The method of claim 12, wherein said antibody is attached to a moiety selected from the group consisting of radioactive moieties and chemotherapeutic moieties.

* * * * *